United States Patent [19]

Soula et al.

[11] 4,314,086
[45] Feb. 2, 1982

[54] PREPARATION OF ALIPHATIC/AROMATIC ETHERS

[75] Inventors: Gerard Soula, Meyzieu; Daniel Michelet, Tassin-la-Demi-Lune, both of France

[73] Assignee: Rhone-Poulenc Industries, Paris, France

[21] Appl. No.: 161,516

[22] Filed: Jun. 20, 1980

[30] Foreign Application Priority Data

Jun. 20, 1979 [FR] France .................. 79 15782

[51] Int. Cl.$^3$ .................. C07C 41/00; C07C 41/16
[52] U.S. Cl. .................. 568/652; 564/221; 564/161; 568/648; 560/61; 560/62; 568/657; 560/81; 562/465; 568/632; 562/471; 260/465 F; 568/633; 260/348.63; 260/505 R; 568/635; 260/340.9 R; 564/505; 568/636; 564/457; 568/642; 568/643; 568/644; 568/646; 568/651; 568/650; 568/640; 568/641; 568/634; 568/649; 568/53; 568/51; 568/655; 568/584; 568/585; 568/33; 568/433; 568/592; 568/315; 564/315; 564/219; 564/215; 564/180; 564/430

[58] Field of Search .................. 568/652, 648, 657, 632, 568/633, 635, 636, 642, 643, 644, 646, 651, 650, 640, 641, 634, 649, 53, 51, 655, 584, 585, 33, 433, 592, 315; 564/315, 219, 215, 180, 430, 221, 161; 560/61, 62, 81; 562/465, 471; 260/465 F, 348.63, 505 R, 340.9 R

[56] References Cited

U.S. PATENT DOCUMENTS 1,966,635  7/1934  Marx et al. .................. 568/652
3,379,755  4/1968  Schultz et al. .................. 568/648 X
3,927,118  12/1975  Ozretich .................. 568/652

FOREIGN PATENT DOCUMENTS 1577240  6/1969  France .................. 568/652

OTHER PUBLICATIONS

McKillop et al, Tetrahedron, vol. 30 (1974) pp. 1379–1382.

*Primary Examiner*—Bernard Helfin
*Attorney, Agent, or Firm*—Burns, Doane, Swecker & Mathis

[57] ABSTRACT

Aliphatic/aromatic ethers are prepared by reacting an aliphatic halide with either an alkali or alkaline earth metal, or ammonium phenolate or naphtholate, in an inert organic solvent, and in the presence of at least one tertiary amine sequestering agent having the formula:

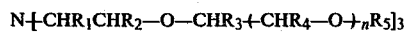

26 Claims, No Drawings

PREPARATION OF ALIPHATIC/AROMATIC ETHERS

CROSS-REFERENCE TO RELATED APPLICATION

Soula and Linguenheld application, Ser. No. 148,590, filed May 12, 1980, and assigned to the assignee hereof.

BACKGROUND OF THE INVENTION

1. Field of the Invention

The present invention relates to an improved process for the preparation of aryl ethers and, more especially, to the preparation of aliphatic/aromatic ethers by reacting an aliphatic halide with a phenolate or a naphtholate.

2. Description of the Prior Art

Processes of the aforenoted type are well known to the prior art. In particular, the synthesis of alkyl/aryl ethers via phase-transfer catalysis, i.e., by reacting an aqueous solution of a phenol with a solution of a haloalkane in a water-immiscible organic solvent, in the presence of a quaternary ammonium compound and an inorganic base, is known. Such process is described, for example, in *Synthesis*, pages 441–456 (1973), and in *Agnew. Chem. Int. Ed. Engl.*, 13, pages 170–179 (1974).

The disadvantage of this type of process is that it requires large amounts of water. Indeed, it is even necessary to treat the waste waters before they are discarded. Furthermore, there are particular cases in which the presence of water is harmful; the water can at least partially degrade one of the reactants; it can also favor secondary reactions such as, for example, reactions involving C-alkylation of polyphenols by chloroalkenyl compounds.

And the French Pat. No. 2,255,279 describes the synthesis of alkyl/aryl ethers by reacting an aliphatic halide with a phenol, in the presence of an alkaline agent, in a polar solvent.

Although this latter process does not require the use of water, same is not suitable for application on an industrial scale because it involves expensive solvents which are difficult to handle.

SUMMARY OF THE INVENTION

Accordingly, a major object of the present invention is the provision of an improved process for the preparation of the aliphatic/aromatic ethers, which process is conspicuously devoid of those disadvantages which to date have characterized the aryl ether/phase-transfer catalysis art.

Briefly, this invention features a process for the preparation of an aliphatic/aromatic ether by reacting, in an organic solvent medium, an aliphatic halide with an alkali metal phenolate or naphtholate, or an alkaline earth metal phenolate or naphtholate, or an ammonium phenolate or naphtholate, characterized in that the reaction is conducted in the presence of at least one sequestering agent having the structural formula:

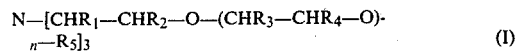

in which n is an integer which is greater than or equal to 0 and less than or equal to about 10 ($0 \leq n \leq 10$), $R_1$, $R_2$, $R_3$ and $R_4$, which are identical or different, each represent a hydrogen atom or an alkyl radical having from 1 to 4 carbon atoms and $R_5$ represents an alkyl or cycloalkyl radical having from 1 to 12 carbon atoms, a phenyl radical or a radical $-C_m-H_{2m}-\phi$ or $C_mH_{2m+1}-\phi-$, in which m is between 1 and 12 ($1 \leq m \leq 12$).

One advantage of the subject process, notably, is the fact that the solvent employed can be an apolar solvent, i.e., a solvent which, on an industrial scale, does not exhibit the disadvantages of the heretofore used solvents. It is even possible to use the aliphatic halide itself as the solvent in certain cases. It is obvious that it is also possible to use a polar solvent, although the industrial advantage is substantially less marked in this particular case.

DETAILED DESCRIPTION OF THE INVENTION

More particularly according to this invention, it has now been determined that the sequestering agent of the formula I forms a complex with the phenolate or the naphtholate, and that the resulting complex is soluble in solvents in which the phenolate or the naphtholate, in the non-complexed state, is insoluble or very sparingly soluble. This complexation exhibits a dual effect; first, it permits the solubilization of the phenolate or naphtholate and therefore enables the reaction to in fact take place; secondly, although not yet completely understood in detail, it would appear that the complexation itself activates the reaction system.

According to a preferred embodiment of the invention, a sequestering agent of the formula (I) is used in which $R_1$, $R_2$, $R_3$ and $R_4$ represent a hydrogen atom or a methyl radical, $R_5$ and n being as above defined.

Among such sequestering agents, it is even more particularly preferred to use those in which n is greater than or equal to 0 and less than or equal to 6 and in which $R_5$ represents an alkyl radical having from 1 to 4 carbon atoms.

The following sequestering agents are noted as illustrative:

[1] tris-(3-oxabutyl)-amine of the formula:

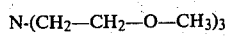

[2] tris-(3,6-dioxaheptyl)-amine of the formula:

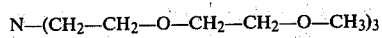

[3] tris-(3,6,9-trioxadecyl)-amine of the formula:

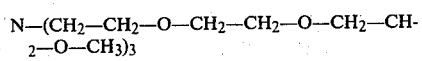

[4] tris-(3,6-dioxaoctyl)amine of the formula:

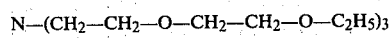

[5] tris-(3,6,9-trioxaundecyl)-amine of the formula:

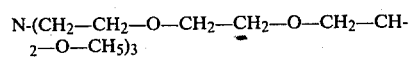

[6] tris-(3,6-dioxanonyl)-amine of the formula:

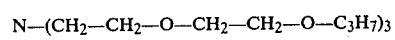

[7] tris-(3,6,9-trioxadodecyl)amine of the formula:

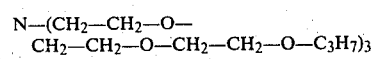

[8] tris-(3,6-dioxadecyl)-amine of the formula:

N—(CH$_2$—CH$_2$—O—CH$_2$—CH$_2$—O—C$_4$H$_9$)$_3$

[9] tris-(3,6,9-trioxatridecyl)-amine of the formula:

N—(CH$_2$—CH$_2$—O—CH$_2$—CH$_2$—O—CH$_2$—CH$_2$—O—C$_4$H$_9$)$_3$

[10] tris-(3,6,9,12-tetraoxatridecyl)-amine of the formula:

N—[CH$_2$—CH$_2$—O—(CH$_2$—CH$_2$—O)$_3$—CH$_3$]$_3$

[11] and tris-(3,6,9,12,15,18-hexaoxanonadecyl)-amine of the formula:

N—[CH$_2$—CH$_2$—O—(CH$_2$—CH$_2$—O)$_5$—CH$_3$]$_3$

The following sequestering agents are also representative:

[12] tris-(3,6-dioxa-4-methylheptyl)-amine of the formula:

N—(CH$_2$CH$_2$—O—CH—CH$_2$—O—CH$_3$)$_3$
                    |
                    CH$_3$ and [13] tris-(3,6,-dioxa-2,4-dimethylheptyl)-amine of the formula:

N—(CH$_2$—CH—O—CH—CH$_2$—O—CH$_3$)$_3$
         |        |
         CH$_3$   CH$_3$

The amine sequestering agents utilized in the process according to the invention are per se known to the prior art. Thus, French Pat. No. 1,302,365 describes the preparation of the tertiary amines N—(CH$_2$—CH$_2$—O—CH$_3$)$_3$ and N—(CH$_2$—CH$_2$—O—CH$_2$—CH$_2$—O—CH$_3$)$_3$ as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in any reaction within the ambit of this invention.

A further advantage of the process according to the invention is that the sequestering agent used can easily be recycled, either by distillation or by extraction.

The aliphatic halides reacted in accordance with the process of the invention have the structural formula:

$$\begin{array}{c} R_6 \\ | \\ X-C-R_7 \\ | \\ R_8 \end{array} \quad (II)$$

in which X represents Cl or Br, and R$_6$, R$_7$ and R$_8$, which are identical or different, each represent a member selected from the group comprising hydrogen, alkyl radicals having from 1 to 24 carbon atoms, alkenyl radicals having from 2 to 24 carbon atoms, alkynyl radicals having from 2 to 24 carbon atoms, optionally substituted phenyl and naphthyl radicals, and the radicals

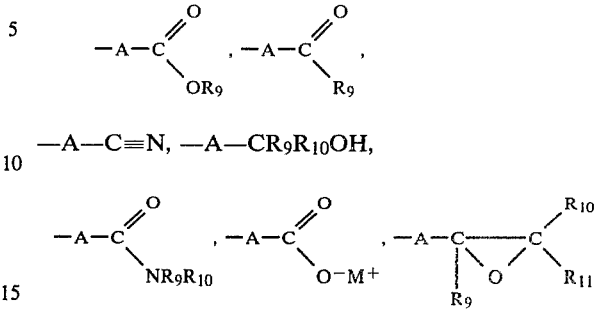

and —A—X, in which A represents a direct valence bond or a saturated or unsaturated hydrocarbon radical having from 1 to 12 carbon atoms, R$_9$, R$_{10}$ and R$_{11}$, which are identical or different, represent an alkyl radical having from 1 to 12 carbon atoms, a phenyl radical or hydrogen, and in which M$^+$ represents an alkali metal cation or alkaline earth metal cation, with X being as above defined.

The phenolates or naphtholates which can be used in the process according to the invention have the structural formula:

Ar(O$^-$M$^+$)$_r$  (III)

in which Ar represents an optionally substituted phenyl or naphthyl radical, M$^+$ represents a cation selected from the group comprising the ammonium cation and the cations derived from alkali metals and alkaline earth metals and r is an integer between 1 and 3 ($1 \leq r \leq 3$).

More particularly, but not exclusively, the invention relates to the reaction of compounds having the structural formulae:

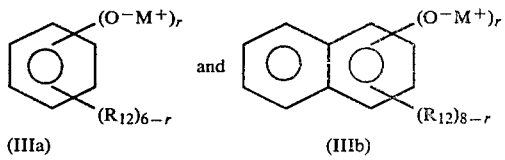

in which r is equal to 1 or 2, the cation or cations M$^+$, which are identical or different, are selected from the group comprising Li$^+$, Na$^+$, K$^+$, NH$_4^+$, Ca$^{2+}$ and Ba$^{2+}$ and the radical or radicals R$_{12}$, which are identical or different, are selected from the group comprising hydrogen, alkyl and cycloalkyl radicals having from 1 to 12 carbon atoms, alkenyl radicals having from 3 to 12 carbon atoms, such as, for example, propenyl, nonyl and dodecyl radicals, the radical —OH, the radicals of the formulae C$_m$H$_{2m+1}\phi$—, C$_m$H$_{2m-1}\phi$— and $\phi$—C$_m$H$_{2m}$—, in which m is an integer between 1 and 12 ($1 \leq m \leq 12$) and in which the phenyl moiety $\phi$ can either be substituted or unsubstituted, alkoxy radicals having from 1 to 12 carbon atoms and phenoxy radicals, the radicals —C$_m$H$_{2m}$—OH and —C$_m$H$_{2m}$OR$_{13}$, in which m is an integer between 1 and 12 ($1 \leq m \leq 12$) and in which R$_{13}$ is an alkyl radical having from 1 to 12 carbon atoms or a phenyl radical, alkylthio radicals having from 1 to 12 carbon atoms and phenylthio radicals, the radicals C$_p$H$_{2p+1-q}$F$_q$, p being between 1 and 4 ($1 \leq p \leq 4$) and q being between 3 and 9 ($3 \leq q \leq 9$), such as, for example, —CF$_3$ and —CH$_2$—CF$_3$, the radicals

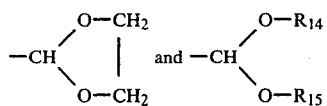

in which R$_{14}$ and R$_{15}$, which are identical or different, each represent an alkyl radical having from 1 to 12 carbon atoms or a phenyl radical, the radicals Cl and F and the radicals —NO$_2$, —NH$_2$, —NHR$_{14}$, —NR$_{14}$R$_{15}$, —SO$_3$M, —CN, —CO$_2$M, —CO$_2$R$_{14}$, —COR$_{14}$, —COH and —SO$_2$R$_{14}$, in which M represents an alkali metal and in which R$_{14}$ and R$_{15}$ are as above defined.

The following compounds are set forth as exemplary of the aliphatic halides of the formula II: CH$_3$—CL, CH$_3$—Br, C$_2$H$_5$—Cl, C$_2$H$_5$—Br, C$_3$H$_7$—Cl, CH$_2$=CH—CH$_2$—Cl, CH$_2$=C(CH$_3$)—CH$_2$—Cl, CH$_3$—C(CH$_3$)$_2$—Cl, C$_2$H$_5$—C(CH$_3$)$_2$—Cl, C$_3$H$_7$—CH(CH$_3$)—Cl, nC$_5$H$_{11}$—Cl, nC$_6$H$_{13}$—Cl, C$_3$H$_7$—CH(C$_2$H$_5$)—Cl, nC$_{10}$H$_{21}$—CL, nC$_{10}$H$_{21}$Br, CH≡C—CH$_2$—Cl, CH$_3$—C≡C—CH$_2$—Cl,

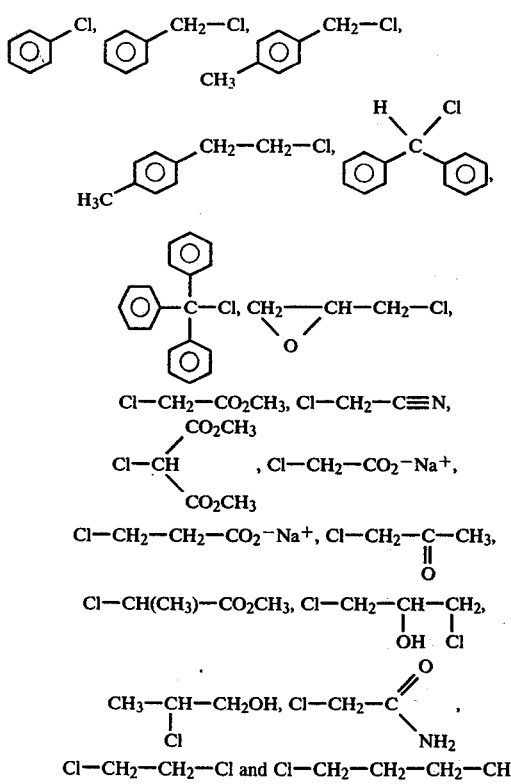

Cl—CH$_2$—CH$_2$—Cl and Cl—CH$_2$—CH$_2$—CH$_2$—CH$_2$—Cl.

The compounds derived from the following phenols and naphthols are set forth as exemplary of the phenolates and naphtholates of the formulae IIIa and IIIb:

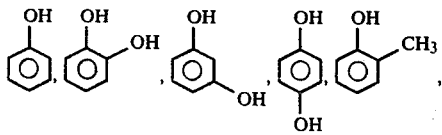

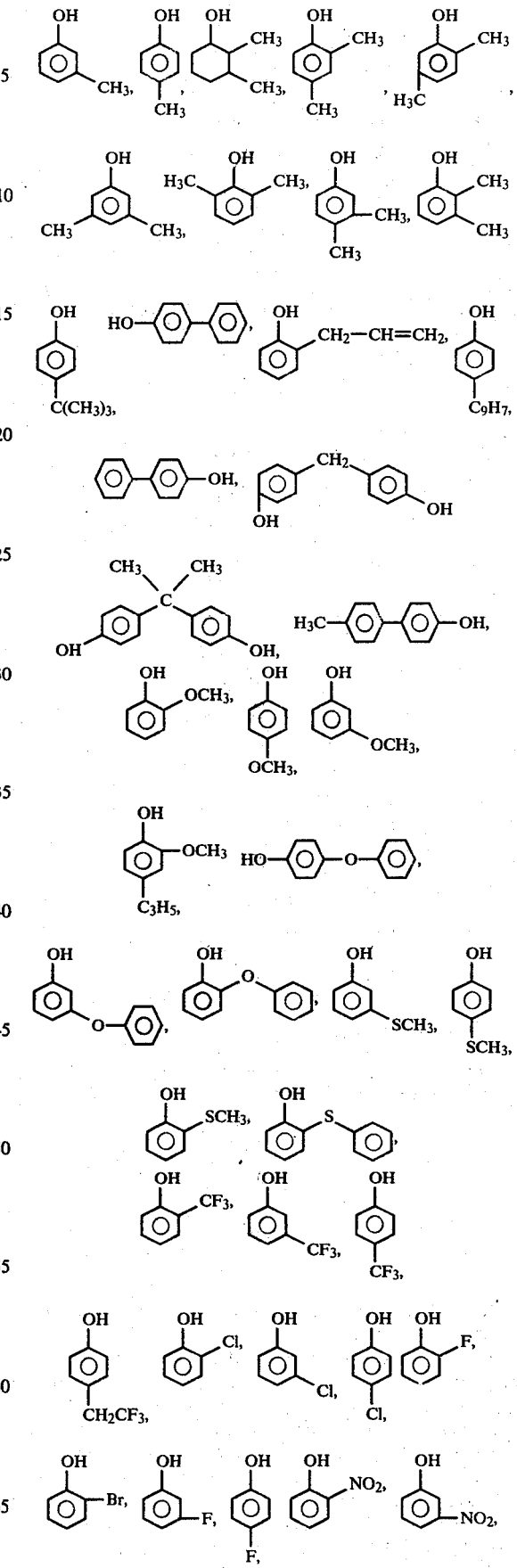

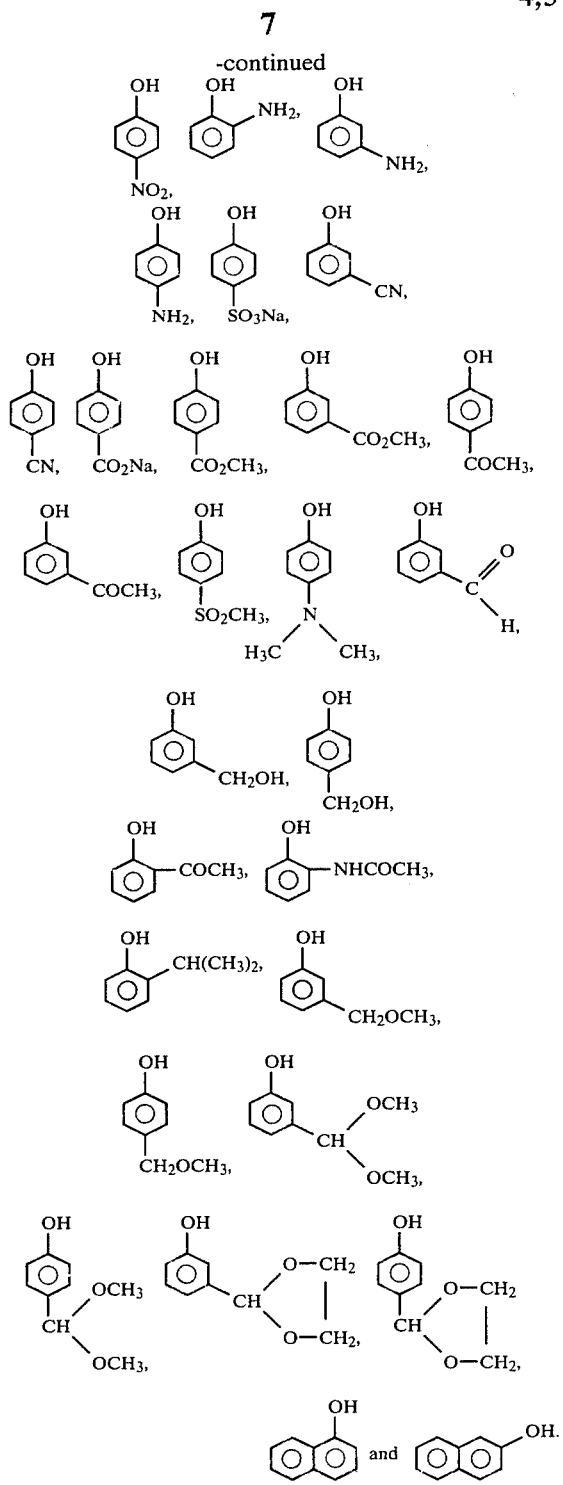

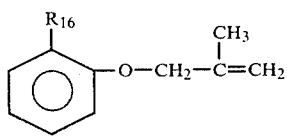

The selection of the most suitable sequestering agent for carrying out the process according to the invention is made with regard to the size of the cation M+. The larger the cation, the greater must be the number of oxygen atoms present in the molecule of the sequestering agent. Thus, if a potassium phenolate is used, tris-(3,6,9-trioxadecyl)-amine is preferred, whereas tris-(3,6-dioxaheptyl)-amine is preferred in the case of the corresponding sodium salt.

If a solvent is used, it must satisfy a certain number of conditions; firstly, it must solubilize the sequestering agent (the latter being soluble in the majority of the customary solvents); it must also be chemically inert vis-a-vis the salts to be dissolved. It must also be noted that, in order to obtain the best results according to the invention, the more pronounced the apolar character of the selected solvent, the more pronounced must be the lipophilic character of the sequestering agent (namely, the greater must be the number of carbon atoms present in the sequestering agent).

Examples of the solvents which can be used within the scope of the process according to the invention are: benzene, toluene, o-, m- and p-xylene, monochlorobenzene, ortho-dichlorobenzene, chloroform, anisole, diphenyl ether, acetonitrile, dichloroethane, chlorobutane, benzyl chloride, nitromethane, dimethylformamide and dimethylacetamide.

The process according to the invention should be carried out at a temperature between about −25° C. and about 150° C.

The process is typically carried out at atmospheric pressure. Of course, pressures which are lower or higher than atmospheric pressure are not excluded by the present invention.

The amount of sequestering agent employed is such that the molar ratio of the sequestering agent to the phenolate or naphtholate is between about 0.5/100 and 15/100; this ratio is preferably between 1/100 and 10/100.

The molar ratio of the halide of the formula II to the phenolate or naphtholate of the formula III is between about 10 and about 0.8. The high values of this ratio correspond to the case where the halide is used as the solvent.

The aliphatic/aromatic ethers prepared in accordance with the process of the invention have the structural formulae:

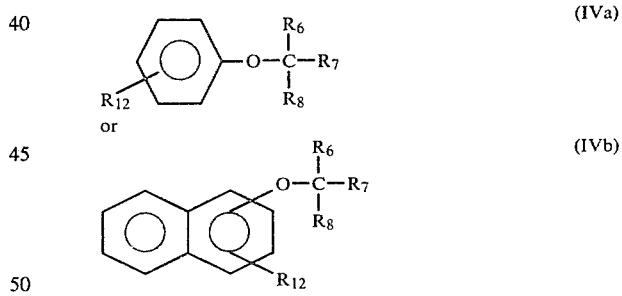

Exemplary of the compounds IVa for which the process according to the invention is particularly suitable are the compounds of the formula:

in which $R_{16}$ represents a radical selected from the group comprising OH, F, Cl, Br, $NO_2$, and alkoxy, alkanoyl (for example $-CO-CH_3$), $-NHCO$—alkyl and alkyl radicals, these radicals preferably having from 1 to 4 carbon atoms, which compounds result from the reaction of an alkali metal salt of the phenol:

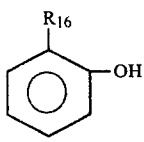

with methallyl chloride.

Additional examples of the compounds IVa and IVb are as follows:

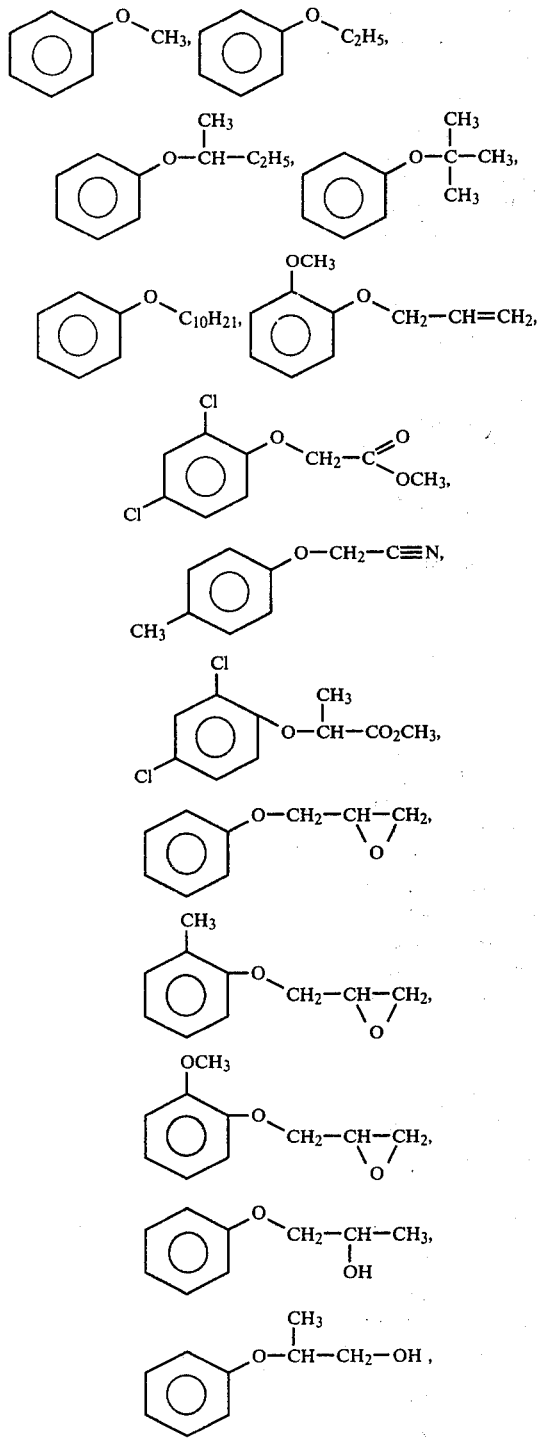

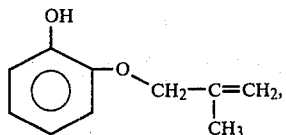

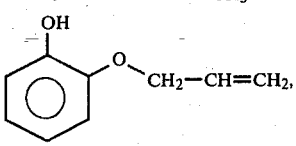

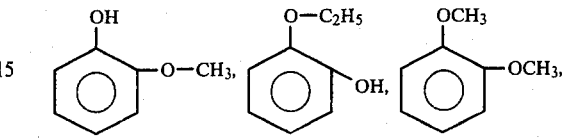

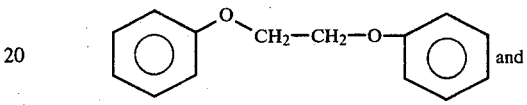

The subject compounds are notable intermediates for the synthesis of plant-protection products or for the preparation of a wide variety of pharmaceutical products.

The sequestering agents used in the process according to the invention can be prepared in the following manner:

These compounds can be prepared by condensing a salt of the formula:

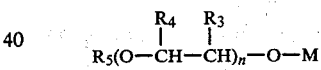

in which $R_3$, $R_4$, $R_5$ and n are as above defined and in which M represents an alkali metal atom selected from among sodium, potassium and lithium, either with an amine having the structural formula:

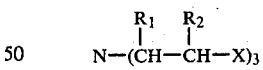

in which $R_1$ and $R_2$ are as defined as above and X represents chlorine or bromine, or with the corresponding hydrochloride or hydrobromide.

The molar ratio alkali metal salt/amine desirably is between about 3 and about 5.

The condensation is carried out at a temperature between 100° and 150° C. for 1 to 15 hours, in the presence of a solvent which can be, for example, chlorobenzene or, preferably the ethylene glycol monoalkyl ether having the formula: $R_5(O\text{—}CHR_4\text{—}CHR_3)_n\text{—}OH$.

The reaction is preferably carried out in such manner that the solution contains from 2 to 5 mols of alkali metal salt per liter of solvent.

The mixture upon completion of the reaction essentially consists of the tertiary amine of the formula:

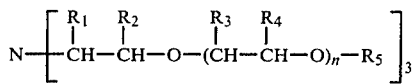

but also contains a small proportion of the corresponding secondary amine:

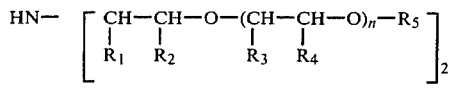

and traces of the primary amine:

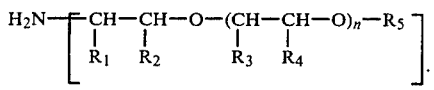

The tertiary, secondary and primary amines are typically present in the ratio 90:8:2, respectively, after distillation.

The aforesaid mixture obtained after a first distillation, i.e., the mixture containing the three different types of amines, can be used directly in the process according to the invention.

For better results consistent with the invention, a more thorough distillation of the above mixture is preferably carried out in order to obtain an essentially pure tertiary amine.

In order to further illustrate the present invention and the advantages thereof, the following specific examples are given, it being understood that same are intended only as illustrative and in nowise limitative.

EXAMPLE 1

Preparation of the n-butyl ether of phenol, having the formula:

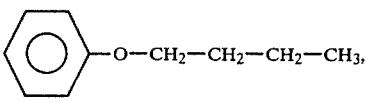

by reacting sodium phenate and n-butyl chloride in chlorobenzene, in the presence of tris-(3,6-dioxaheptyl)-amine.

200 cm$^3$ of anhydrous chlorobenzene, 11.6 g (1 mol) of anhydrous sodium phenate, 12 g (0.13 mol) of n-butyl chloride and 1.6 g (0.005 mol) of tris-(3,6-dioxaheptyl)-amine were successively introduced into a 500 ml three-necked round-bottomed flask.

The reaction medium was stirred and heated at 80° C. The yield of the reaction was 78% after 29 hours and 98% after 46 hours.

COMPARATIVE EXAMPLE

Under the same operating conditions as above, but in the absence of the tris-(3,6-dioxaheptyl)-amine, no formation of the n-butyl ether of phenol was observed.

EXAMPLE 2

Preparation of 3-phenoxyprop-1-ene having the formula:

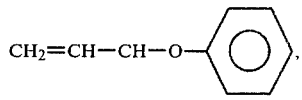

from sodium phenate and allyl chloride in chlorobenzene, in the presence of tris-(3,6-dioxaheptyl)amine.

200 cm$^3$ of anhydrous chlorobenzene, 11.6 g (0.1 mol) of anhydrous sodium phenate, 10 g (0.13 mol) of allyl chloride and 1.6 g (0.005 mol) of tris-(3,6-dioxaheptyl)-amine were successively introduced into a 500 ml three-necked round-bottomed flask equipped with a mechanical stirrer, a thermometer and a reflux condenser.

The reaction medium was heated at 45° C.

The yield was 47% after a reaction time of 6 hours and 99% after 23 hours.

COMPARATIVE EXAMPLE

In the absence of tris-(3,6-dioxaheptyl)-amine, under the same operating conditions as above, no formation of the allyl ether was observed.

EXAMPLE 3

Preparation of the glycidyl ether of ortho-cresol, having the formula:

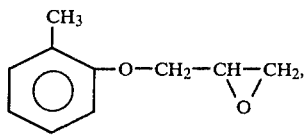

by reacting sodium ortho-cresolate and epichlorohydrin,

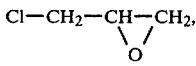

in tetrahydrofuran, in the presence of tris-(3,6-dioxaoctyl)amine.

300 cm$^3$ of anhydrous tetrahydrofuran, 65 g (0.5 mol) of sodium o-cresolate, 51 g (0.55 mol) of freshly distilled epichlorhydrin and 9.1 g (0.025 mol) of tris-(3,6-dioxaoctyl)-amine were successively introduced into a 500 ml three-necked round-bottomed flask equipped with a mechanical stirrer, a thermometer and a reflux condenser. The reaction medium was heated at 67° C. The degree of conversion was 51% after a reaction time of 5 hours.

COMPARATIVE EXAMPLE

In the absence of tris-(3,6-dioxaoctyl)-amine, under the same operating conditions as above, the degree of conversion was 24% after a reaction time of 5 hours.

EXAMPLE 4

Preparation of the glycidyl ether of guaiacol by reacting sodium guaiacolate and epichlorohydrin (the epichlorohydrin serving as the solvent), in the presence of tris-(3,6-dioxaoctyl)-amine.

Preparation of sodium guaiacolate 341 g (2.75 mols) of guaiacol, 300 g of water and 700 g of toluene were introduced into a 3 liter three-necked reactor equipped with a mechanical stirrer, a condenser and a dropping funnel.

Using the dropping funnel, a 33% strength aqueous solution of sodium hydroxide (300 g, namely 2.5 mols, of sodium hydroxide) was slowly added, care being taken to maintain the termperature between 45° C. and 55° C. The mixture was stirred for 2 hours and then permitted to separate out. The aqueous layer was concentrated until the sodium guaiacolate precipitated. After cooling, the crystals of guaiacolate were filtered off and then dried by azeotropic distillation in the presence of toluene.

After filtration, the solids were dried at 80°–90° C. under a pressure of 20 mm Hg for 8 hours. The yield was 95%.

Preparation of glycidyl ether of guaiacol 740 g of epichlorhydrin, which had been distilled and maintained, over sieves, and 18.3 g (0.05 mol) of tris(3,6-dioxaoctyl)-amine were introduced into a 2 liter four-necked round-bottomed flask equipped with a mechanical stirrer, a reflux condenser fitted with a CaCl₂ trap, and a thermometer. The mixture was heated to 118° C. under a stream of nitrogen. The sodium guaiacolate was introduced in ten 0.1 mol portions at 15-minute intervals. After the last portion had been added, heating was maintained for a further 15 minutes.

The mixture was subsequently permitted to cool and the NaCl formed [60 g (theory=58 g)] was filtered off; the epichlorohydrin was recovered by means of a rotary evaporator under a pressure of 5 mm Hg (temperature of the oil bath: 80° C.).

The resulting crude product (205 g) was distilled; the main fraction was composed of the glycidyl ether of guaiacol (θ=96°–109° C. under a pressure of 0.1 mm Hg). The amount of product collected corresponded to a yield of 93%, relative to the guaiacolate introduced.

A second fraction, which distilled between 130° C. and 160° C. under a pressure of 0.2 mm Hg, was recovered; this fraction consisted of 14 g of tris-(3,6-dioxaoctyl)-amine (77% of the sequestering agent employed).

COMPARATIVE EXAMPLE

Without the tris-(3,6-dioxaoctyl)-amine, the yield of the reaction was 68%.

EXAMPLE 5

Preparation of the glycidyl ether of guaiacol, having the formula:

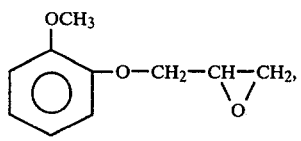

by reacting sodium guaiacolate, having the formula:

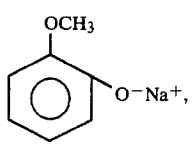

and epichlorohydrin in acetonitrile, in the presence of tris-(3,6-dioxaoctyl)-amine.

300 cm³ of anhydrous acetonitrile, 73 g (0.5 mol) of sodium guaiacolate, 51 g (0.55 mol) of epichlorohydrin and 9.1 g (0.025 mol) of tris-(3,6-dioxaoctyl)-amine were successively introduced into a 500 ml three-necked round-bottomed flask equipped with a reflux condenser, a thermometer and a mechanical stirrer.

The reaction mixture was heated at the reflux temperature of the acetonitrile, without stirring. The degree of conversion was 60% after a reaction time of 5 hours.

COMPARATIVE EXAMPLE

Under the same operating conditions as above, but in the absence of tris-(3,6-dioxaoctyl)-amine, the degree of conversion was 25% after a reaction time of 5 hours.

EXAMPLE 6

Preparation of the monoether having the formula:

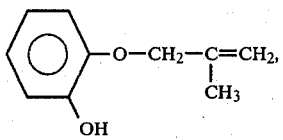

by reacting sodium pyrocatecholate, having the formula:

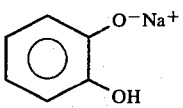

and methallyl chloride,

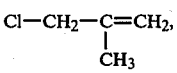

in toluene, in the presence of tris-(3,6-dioxaoctyl)amine.

70 cm³ of toluene, 6.6 g (0.05 mol) of sodium pyrocatecholate, 9.1 g (0.1 mol) of distilled methallyl chloride and 1.5 g (0.005 mol) of tris-(3,6-dioxaoctyl)-amine were successively introduced into a 250 ml three-necked round-bottomed flask equipped with a mechanical stirrer, a reflux condenser and a thermometer. A stream of argon was passed therethrough and the reaction mixture was heated at 100° C. for 5 hours. The degree of conversion of the sodium pyrocatecholate was 55%. The yield of the monoether formed was 92%.

COMPARATIVE EXAMPLE

Under the same conditions as above, but in the absence of tris-(3,6-dioxaoctyl)-amine, the degree of conversion was less than 5%.

EXAMPLES 7 to 10

Preparation of the monoether having the formula:

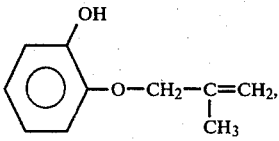

by reacting sodium pyrocatecholate and methallyl chloride in various solvents and in the presence of tris-(3,6-dioxaoctyl)-amine.

The procedure of Example 6 was followed, the toluene being replaced by chlorobenzene (Examples 7 and 8), anisole (Example 9) and acetonitrile (Example 10). The results of these examples are reported in Table I.

TABLE I

| Example | Solvent | Duration | Degree of conversion | Selectivity |
|---|---|---|---|---|
| 7 | chlorobenzene | 4 hours 15 minutes | 67% | 95% |
| 8 | chlorobenzene | 5 hours 55 minutes | 74% | 93% |
| 9 | anisole | 6 hours 30 minutes | 73.5% | 94.5% |
| 10 | acetonitrile | 10 hours 30 minutes | 67.5% | 90% |

EXAMPLES 11 and 12

Preparation of the monoether having the formula:

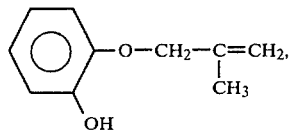

by reacting sodium pyrocatecholate and methallyl chloride in various solvents and in the presence of tris-(3,6-dioxaoctyl)-amine.

The procedure of Example 6 was followed, the tris-(3,6-dioxaoctyl)-amine being replaced by tris-(3,6-dioxaheptyl)-amine and the toluene being replaced by chlorobenzene (Example 11) and anisole (Example 12).

The results are reported in Table II.

TABLE II

| Example | Solvent | Duration | Degree of conversion | Selectivity |
|---|---|---|---|---|
| 11 | chlorobenzene | 2 hours 30 minutes | 39% | 95% |
| 12 | anisole | 3 hours 30 minutes | 66% | 93% |

EXAMPLE 13

Reaction of sodium pyrocatecholate with ethyl bromide in acetonitrile, in the presence of tris-(3,6-dioxaheptyl)-amine.

200 ml of acetonitrile, 13.2 g (0.1 mol) of sodium pyrocatecholate, 16.4 g (0.15 mol) of ethyl bromide and 1.6 g (0.005 mol) of tris-(3,6-dioxaheptyl)-amine were successively introduced into a 500 ml three-necked round-bottomed flask equipped with a mechanical stirrer, a thermometer and a reflux condenser. The mixture was stirred and heated at 40° C. for 8 hours. The degree of conversion of the sodium pyrocatecholate was 70%.

COMPARATIVE EXAMPLE

Under the same operating conditions as above, but in the absence of tris-(3,6-dioxaheptyl)-amine, the degree of conversion of the sodium pyrocatecholate was only 8%.

EXAMPLE 14

Reaction of sodium pyrocatecholate with ethyl bromide in acetonitrile, in the presence of tris-(3,6,9-trioxadecyl)-amine.

200 ml of acetonitrile, 14.8 g (0.1 mol) of potassium pyrocatecholate, 16.4 g (0.15 mol) of ethyl bromide and 2.27 g (0.005 mol) of tris-(3,6,9-trioxadecyl)-amine were introduced into the equipment defined above. The mixture was stirred and heated at 40° C. for 8 hours. The degree of conversion of the potassium pyrocatecholate was 87%.

EXAMPLE 15

Synthesis of methyl 2-(2-methyl-4-chlorophenoxy)-propionate by reacting sodium 2-methyl-4-chlorophenate with methyl 2-chloropropionate in toluene, in the presence of tris-(3,6-dioxaoctyl)-amine.

250 cm³ of toluene, 32.9 g (0.2 mol) of sodium 2-methyl-4-chlorophenate, 24.5 g (0.2 mol) of methyl 2-chloropropionate and 1.8 g (0.005 mol) of tris-(3,6-dioxaoctyl)-amine were successively introduced into a 500 ml three-necked round-bottomed flask equipped with a mechanical stirrer, a thermometer and a reflux condenser. The mixture was heated at 50° C. for 7 hours and then cooled to 20° C. 100 cm³ of water were then added in order to remove the salts formed and the unconverted sodium chlorocresolate. The organic phase was dried over silica gel and the toluene was then evaporated off. The methyl 2-(2-methyl-4-chlorophenoxy)-propionate was recovered by distillation ($\theta=91°-93°$ C. under a pressure of 0.5 mm Hg). The yield of the reaction was 74%.

COMPARATIVE EXAMPLE

Under the same operating conditions as above, but in the absence of tris-(3,6-dioxaoctyl)-amine, the yield of the reaction was 12%.

EXAMPLE 16

Preparation of tris-(3,6-dioxaoctyl)-amine:

(a) 450 g (5 mols) of 2-ethoxyethanol were introduced into a one liter three-necked round-bottomed flask equipped with a mechanical stirrer, a thermometer and a condenser. 23 g (1 mol) of sodium were added over the course of 3 hours, while maintaining the temperature of the mixture at 40° C.

(b) 51.6 g (namely, 0.215 mol) of tris-(2-chloroethyl)-amine hydrochloride was added to the above mixture. The mixture was subsequently heated at the reflux temperature of the 2-ethoxyethanol for 12 hours and the solvent was then distilled under reduced pressure. The excess sodium 2-ethoxyethanolate was neutralized by adding 12 cm³ of aqueous HCl (10 N).

The sodium chloride formed was filtered off and the solution was distilled. The tris-(3,6-dioxaoctyl)-amine distilled between 200° C. and 210° C. under a pressure of 1 mm Hg. The yield was 68%.

EXAMPLE 17

Preparation of tris-(3,6-dioxaheptyl)-amine.

(a) 380 g (5 mols) of 2-methoxyethanol were introduced into a one liter three-necked round-bottomed flask equipped with a mechanical stirrer, a thermometer and a condenser. 23 g (1 mol) of sodium were added over the course of 3 hours, while maintaining the temperature of the mixture at 40° C.

(b) 51.6 g (namely, 0.215 mol) of tris-(2-chloroethyl)-amine hydrochloride were added to the above mixture. The mixture was subsequently heated at the reflux temperature of the 2-methoxyethanol (125° C.) for 12 hours and the solvent was then distilled under reduced pressure. The excess sodium 2-ethoxyethanolate was neutralized by adding 11.6 cm³ of aqueous HCl (10 N). The sodium chloride was filtered off and the solution was distilled.

EXAMPLE 18

Preparation of tris-(3,6,,9-trioxadecyl)-amine:

600 g, namely 5 mols, of diethylene glycol monomethyl ether (3,6-dioxaheptan-1-ol) were introduced into a one liter three-necked round-bottomed flask equipped with a mechanical stirrer, a condenser and a thermometer, and 23 g (1 mol) of sodium were then introduced in small portions in order to form sodium 3,6-dioxaheptanolate.

When the sodium has been totally converted, 51.8 g (namely, 0.215 mol) of tris-(2-chloroethyl)-amine hydrochloride were added. The mixture was heated at 130° C. for 8 hours, under stirring, and then cooled, and the excess sodium alcoholate was neutralized with a 10% strength aqueous solution of hydrochloric acid. The 3,6-dioxaheptan-1-ol was removed by distillation at 130° C. under a pressure of 20 mm Hg. The resulting mixture was filtered in order to remove the sodium chloride, and the product was then distilled. 82 g of tris-(3,6,9-trioxadecyl)-amine, which distilled at 189° C. under a pressure of 0.1 mm Hg, were thus obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an aliphatic-/aromatic ether, comprising reacting an aliphatic halide with an alkali or alkaline earth metal, or ammonium phenolate or naphtholate, in the presence of a catalytic amount of at least one tertiary amine sequestering agent having the formula:

$$N-[-CHR_1-CHR_2-O-(-CHR_3-CHR_4-O-)_{\overline{n}}R_5]_3 \quad (I)$$

in which n is an integer which is greater than or equal to 0 and less than or equal to about 10, $R_1$, $R_2$, $R_3$ and $R_4$, which are identical or different, each represent a hydrogen atom or an alkyl radical having from 1 to 4 carbon atoms and $R_5$ represents an alkyl or cycloalkyl radical having from 1 to 12 carbon atoms, a phenyl radical or a radical $-C_mH_{2m}-\phi$ or $C_mH_{2m+1}-\phi-$, wherein $\phi$ is phenyl and in which m ranges from 1 to 12.

2. The process as defined by claim 1, wherein the reaction is conducted in the presence of an inert organic solvent.

3. The process as defined by claim 2, wherein the formula (I), $R_1$, $R_2$, $R_3$ and $R_4$ are each hydrogen or methyl.

4. The process as defined by claims 2 or 3, wherein the formula (I), n is an integer which is greater than or equal to 0 and less than or equal to 6.

5. The process as defined by claims 2 or 3, wherein the formula (I), $R_5$ is an alkyl radical having from 1 to 4 carbon atoms.

6. The process as defined by claims 2 or 3, wherein the formula (I), $R_1$, $R_2$, $R_3$ and $R_4$, which are identical or different, are each hydrogen or methyl, n is an integer which is greater than or equal to 0 and less than or equal to 6 and $R_5$ is an alkyl radical having from 1 to 4 carbon atoms.

7. The process as defined by claim 6, wherein the tertiary amine of the formula (I) is tris-(3,6-dioxaheptyl)-amine of the formula:

$$N-(CH_2-CH_2-O-CH_2-CH_2-O-CH_3)_3.$$

8. The process as defined by claim 6, wherein the tertiary amine of the formula (I) is tris-(3,6,9-trioxadecyl)-amine of the formula:

$$N-(CH_2-CH_2-O-CH_2-CH_2-O-CH_2-CH_2-O-CH_3)_3.$$

9. The process as defined by claim 6, wherein the tertiary amine of the formula (I) is tris-(3,6-dioxaoctyl)-amine of the formula:

$$N-(CH_2-CH_2-O-CH_2-CH_2-O-C_2H_5)_3.$$

10. The process as defined by claim 2, wherein the tertiary amine of the formula (I) is selected from the group consisting of tris-(3-oxabutyl)-amine, tris-(3,6-dioxahetpyl)-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6,9,12-tetraoxatridecyl)-amine, tris-(3,6,9,12,15,18-hexaoxanonadecyl)-amine, tris-(3,6-dioxa-4-methylheptyl)-amine and tris-(3,6,-dioxa-2,4-dimethylheptyl)-amine.

11. The process as defined by claim 2, said inert organic solvent being an apolar solvent.

12. The process as defined by claims 1 or 2, wherein the aliphatic halide reacted has the structural formula:

$$\begin{array}{c} R_6 \\ | \\ X-C-R_7 \\ | \\ R_8 \end{array} \quad (II)$$

in which X represents Cl or Br, and $R_6$, $R_7$ and $R_8$, which are identical or different, each represent a member selected from the group consisting of hydrogen, alkyl radicals having from 1 to 24 carbon atoms, alkenyl radicals having from 2 to 24 carbon atoms, alkynyl radicals having from 2 to 24 carbon atoms, substituted and unsubstituted phenyl and naphthyl radicals, and the radicals

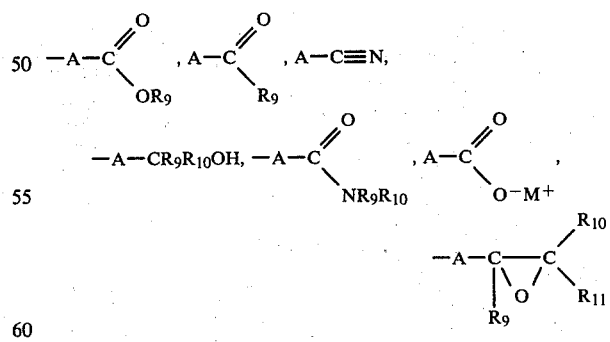

and $-A-X$, in which A represents a direct valence bond or a saturated or unsaturated hydrocarbon radical, $R_9$, $R_{10}$ and $R_{11}$, which are identical or different, represent an alkyl radical having from 1 to 12 carbon atoms, a phenyl radical or hydrogen, and in which $M^+$ represents an alkali metal cation or alkaline earth metal cation, and X is as above defined.

13. The process as defined by claims 1 or 2, wherein the phenolate or naphtholate reacted has the structural formula:

$$\text{(IIIa)} \quad \underset{(R_{12})_{6-r}}{\underset{|}{\bigcirc}}(O^-M^+)_r \quad \text{or} \quad \text{(IIIb)} \quad \underset{(R_{12})_{8-r}}{\underset{|}{\bigcirc\bigcirc}}(O^-M^+)_r$$

in which r is equal to 1 or 2, the cation or cations $M^+$, which are identical or different, are selected from the group consisting of $Li^+$, $Na^+$, $K^+$, $NH_4^+$, $Ca^{2+}$ and $Ba^{2+}$ and the radical or radicals $R_{12}$, which are identical or different, are selected from the group consisting of hydrogen, alkyl and cycloalkyl radicals having from 1 to 12 carbon atoms, alkenyl radicals having from 3 to 12 carbon atoms, the radical —OH, the radicals of the formulae $C_mH_{2m-1}\phi$—, $C_mH_{2m-1}\phi$— and $\phi$—$C_mH_{2m}$—, in which m is an integer of from 1 to 12 and $\phi$ comprises aphenyl moiety, alkoxy radicals having from 1 to 12 carbon atoms and phenoxy radicals, the radicals —$C_mH_{2m}$—OH and —$C_mH_{2m}OR_{13}$, in which m is an integer of from 1 to 12 and in which $R_{13}$ is an alkyl radical having from 1 to 12 carbon atoms and phenylthio radicals, the radicals $C_pH_{2p+1-q}F_q$, p ranging from 1 to 4 and q ranging from 3 to 9, the radicals $$-CH\underset{O-CH_2}{\overset{O-CH_2}{\diagup}}\Big| \quad \text{and} \quad -CH\underset{O-R_{15}}{\overset{O-R_{14}}{\diagup}}$$

in which $R_{14}$ and $R_{15}$, which are identical or different, each represent an alkyl radical having from 1 to 12 carbon atoms or a phenyl radical, the radicals Cl and F and the radicals —$NO_2$, —$NH_2$, —$NHR_{14}$, —$NR_{14}R_{15}$, —$SO_3M$, —CN, —$CO_2M$, —$CO_3R_{14}$, —$COR_{14}$, —COH and —$SO_2R_{14}$, in which M represents an alkali metal and in which $R_{14}$ and $R_{15}$ are as above defined.

14. The process as defined by claim 13, said phenolate or naphtholate having the structural formula (IIIa).

15. The process as defined by claim 13, said phenolate or naphtholate having the structural formula (IIIb).

16. The process as defined by claim 2, wherein the reaction is conducted in the presence of a solvent selected from the group consisting of benzene, toluene, o-, m- and p-xylene, monochlorobenzene, ortho-dichlorobenzene, chloroform, anisole, diphenyl ether, acetonitrile, dichloroethane, chlorobutane, benzyl chloride, nitromethane, dimethylformamide and dimethylacetamide.

17. The process as defined by claims 1 or 2, wherein the reaction is conducted at a temperature between about $-25°$ C. and about $150°$ C.

18. The process as defined by claim 2, said aliphatic halide reactant comprising the inert organic solvent.

19. The process as defined by claims 1 or 2, wherein the amount of sequestering agent having the formula I used is such that the molar ratio of the sequestering agent to the phenolate or naphtholate ranges from about 0.5/100 to 15/100.

20. The process as defined by claim 19, wherein said molar ratio of the sequestering agent to the phenolate or naphtholate ranges from 1/100 to 10/100.

21. The process as defined by claim 19, wherein the molar ratio of the aliphatic halide to the phenolate or naphtholate ranges from about 10 to about 0.8.

22. A process as defined by claims 1 or 2 for the preparation of an aliphatic/aromatic ether having the structural formula:

$$\underset{}{\bigcirc}\overset{R_{16}}{\underset{}{\big|}}-O-CH_2-\underset{CH_3}{\overset{|}{C}}=CH_2$$

in which $R_{16}$ represents a radical selected from the group consisting of the OH radical, alkoxy radicals having from 1 to 4 carbon atoms, F, Cl, Br and $NO_2$ radicals, alkanoyl radicals having from 1 to 4 carbon atoms, and alkyl CONH— and alkyl radicals having from 1 to 4 carbon atoms, comprising reacting an alkali metal salt of the phenol of the formula:

$$\underset{}{\bigcirc}\overset{R_{16}}{\underset{}{\big|}}-OH$$

in which $R_{16}$ is as above defined with methallyl chloride, in the presence of at least one sequestering agent having the formula:

$$N\text{-}[CHR_1-CHR_2O\text{-}(CHR_3-CHR_4-O)_nR_5]_3 \quad (I)$$

in which n is an integer which is greater than or equal to 0 and less than or equal to about 10, $R_1$, $R_2$, $R_3$ and $R_4$, which are identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical —$C_mH_{2m}$—$\phi$ or $C_mH_{2m+1}$—$\phi$—, in which m ranges from 1 to 12 and $\phi$ is phenyl.

23. The process as defined by claim 2 for the preparation of an aliphatic/aromatic ether having the structural formula:

$$\underset{}{\bigcirc}\overset{OH}{\underset{}{\big|}}-O-CH_2-\underset{CH_3}{\overset{|}{C}}=CH_2$$

comprising reacting sodium pyrocatecholate with methallyl chloride in an organic solvent medium, in the presence of tris-(3,6-dioxaoctyl)-amine of the formula:

$$N-(CH_2CH_2-O-CH_2-CH_2-O-C_2H_5)_3.$$

24. The process as defined by claim 23, wherein the reaction is carried out in the presence of a solvent selected from the group consisting of toluene, chlorobenzene, anisole and acetonitrile.

25. The process as defined by claim 23, comprising reacting sodium pyrocatecholate with methallyl chloride in an organic solvent medium, in the presence of tris-(3,6-dioxaheptyl)-amine of the formula:

$$N-(CH_2-CH_2-O-CH_2-CH_2-O-CH_3)_3.$$

26. The process as defined by claim 25, wherein the reaction is carried out in the presence of a solvent selected from the group consisting of chlorobenzene and anisole.

* * * * *